United States Patent
Risch (10) Patent No.: US 11,957,857 B2
(45) Date of Patent: Apr. 16, 2024

(54) PROCESS FOR ASSEMBLING A PROTECTIVE SHEATH ON A DRUG-COATED BALLOON CATHETER

(71) Applicant: BIOTRONIK AG, Bülach (CH)

(72) Inventor: Fabian Risch, Doerflingen (CH)

(73) Assignee: BIOTRONIK AG, Buelach (CH)

(*) Notice: Subject to any disclaimer, the term of this patent is extended or adjusted under 35 U.S.C. 154(b) by 354 days.

(21) Appl. No.: 17/294,925

(22) PCT Filed: Nov. 19, 2019

(86) PCT No.: PCT/EP2019/081776
§ 371 (c)(1),
(2) Date: May 18, 2021

(87) PCT Pub. No.: WO2020/109076
PCT Pub. Date: Jun. 4, 2020

(65) Prior Publication Data
US 2022/0001152 A1    Jan. 6, 2022

(30) Foreign Application Priority Data
Nov. 27, 2018  (DE) ............................ 102018129918

(51) Int. Cl.
*A61M 25/10*     (2013.01)
*A61F 2/95*      (2013.01)
(Continued)

(52) U.S. Cl.
CPC ....... *A61M 25/1029* (2013.01); *A61F 2/9522* (2020.05); *A61F 2/958* (2013.01);
(Continued)

(58) Field of Classification Search
CPC ....... B29L 2031/7543; A61M 2207/10; A61M 2250/0067; A61M 2240/001; A61M 2025/1031; A61M 2025/105; A61M 2025/1081; A61M 25/1029; A61M 25/1027; B29C 63/18; B29C 63/0056;
(Continued)

(56) References Cited

U.S. PATENT DOCUMENTS

| 5,350,361 A | 9/1994 | Tsukashima et al. |
| 2004/0093005 A1 | 3/2004 | Durcan |

(Continued)

OTHER PUBLICATIONS

International Search Report and Written Opinion from the corresponding International Patent Application No. PCT/EP2019/081776, dated Mar. 4, 2020.

*Primary Examiner* — Moshe Wilensky
(74) *Attorney, Agent, or Firm* — Greer, Burns & Crain, Ltd.; Steven P. Fallon (57) ABSTRACT

A process for arranging a protective sheath on a drug-coated balloon catheter in a machine. The protective sheath is transported via a transport system into a holding device. A drug coated area of the balloon catheter from contact with the machine. The protective sheath is arranged on a drug-coated area of the balloon catheter by machine relative motion between the balloon catheter and the protective sheath. The protecting can be placing at least one first and one second flexible film between the balloon catheter and a guide of the machine during the relative motion or can be holding the balloon catheter at a position on the catheter away from the drug-coated area during the relative motion.

17 Claims, 6 Drawing Sheets

(51) Int. Cl.
*A61F 2/958* (2013.01)
*B29C 63/00* (2006.01)
*B29C 63/18* (2006.01)
*B29L 31/00* (2006.01)

(52) U.S. Cl.
CPC .......... *B29C 63/0056* (2013.01); *B29C 63/18* (2013.01); *A61F 2250/0067* (2013.01); *A61M 2025/1031* (2013.01); *A61M 2025/105* (2013.01); *A61M 2025/1081* (2013.01); *A61M 2207/10* (2013.01); *B29L 2031/7543* (2013.01)

(58) Field of Classification Search
CPC .... A61F 2/07; A61F 2/82; A61F 2/958; A61F 2/9522
See application file for complete search history.

(56) References Cited

U.S. PATENT DOCUMENTS

| | | |
|---|---|---|
| 2012/0059316 A1 | 3/2012 | Owens et al. |
| 2015/0246203 A1 | 9/2015 | Ciurea et al. |

PROCESS FOR ASSEMBLING A PROTECTIVE SHEATH ON A DRUG-COATED BALLOON CATHETER

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/081776, which was filed Nov. 19, 2019, which application claimed priority from German Application Serial Number 10 2018 129 918, which was filed Nov. 27, 2018.

FIELD OF THE INVENTION

This invention relates to a process for arranging a protective sheath on a balloon catheter, in particular on a drug-coated balloon catheter.

At the present time, in the case of non-drug-coated balloon catheters, protective sheaths are put on the balloon catheter by machine, e.g., by rollers.

When processing drug-coated balloon catheters, it is necessary to prevent cross contamination. To accomplish this, the components that come in contact with the drug must either be cleaned or exchanged after every product. This makes machine processing complicated and cost-intensive.

This is accomplished by a process having the features of claim 1. Advantageous embodiments of this aspect of the invention are indicated in the corresponding subordinate claims and are described below.

SUMMARY OF THE INVENTION

A process for arranging a protective sheath on a drug-coated balloon catheter in a machine. The protective sheath has a wall circling in a peripheral direction and surrounding an interior of the protective sheath. The protective sheath is transported via a transport system into a holding device. A drug coated area of the balloon catheter from contact with the machine. The protective sheath is arranged on a drug-coated area of the balloon catheter by machine relative motion between the balloon catheter and the protective sheath. The protecting can be placing at least one first and one second flexible film between the balloon catheter and a guide of the machine during the relative motion or can be holding the balloon catheter at a position on the catheter away from the drug-coated area during the relative motion.

BRIEF DESCRIPTION OF THE DRAWINGS

Sample embodiments of the invention and features and advantages of this invention are explained below using the figures. The figures are as follows:

FIGS. 1 through 3 an embodiment of the inventive process or an inventive device for arranging a protective sheath on a drug-coated area (e.g., stent or balloon) of a balloon catheter; and FIG. 4 an alternative embodiment of the inventive process or an inventive device.

DETAILED DESCRIPTION OF THE PREFERRED EMBODIMENTS

The drug-coated area created via the preferred process can be, e.g., a drug-coated balloon of the balloon catheter. Furthermore, the drug-coated area can also be a drug-coated stent that is crimped onto a balloon of the balloon catheter.

The wall of the protective sheath can be a continuous wall. Alternatively, however, the wall can also have interruptions in the form of slots or holes, as long as the wall still circles in the peripheral direction.

One embodiment of the process provides that the guide for the balloon catheter have at least one contact element. Such a contact element can have at least one point of contact. In principle, the number of contact elements of the guide is not limited, and can also consist of or include multiple elements. A preferred embodiment provides that the guide for the balloon catheter have at least one first and one opposite second contact element, the first contact element being pressed against the balloon catheter with the first film laid between them, and the second contact element being pressed against the balloon catheter with the second film laid between them, and the relative motion involving the balloon catheter being moved relative to the protective sheath, which is at rest, and inserted into the interior of the protective sheath. Alternatively, it is also possible for the protective sheath to be moved over the balloon catheter, which is at rest, causing the latter to be introduced into the interior of the protective sheath.

Furthermore, one embodiment of the process provides that the first contact element be a rotatable first roller, and that the second contact element be a rotatable second roller.

Furthermore, one embodiment of the process provides that for the contact elements to press against the balloon catheter (with the respective film between), they be moved out of a first position toward one another into a second position, in which the two contact elements press against the balloon catheter (with the respective film between) and guide it.

One embodiment of the process provides that the balloon catheter be moved relative to the protective sheath by an advancement of the respective film. Alternatively or additionally, the balloon catheter can be moved by the respective roller, which is rotated by a drive.

For the case in which the balloon catheter is moved only by the advancement of the film, the pair of rollers only has the function of a guide. In this case, instead of the two contact elements or rollers it is also possible to use other guides (e.g., a funnel-shaped guide or something similar).

A preferred embodiment of the process further provides that the first film be moved along the first roller with an advancement speed that corresponds to a rotational speed of the first roller, and that the second film be moved along the second roller with an advancement speed that corresponds to a rotational speed of the second roller. This can advantageously ensure that the drug-coated area only comes in contact with a fresh, uncontaminated part of the respective film.

One embodiment of the process further provides that the protective sheath be held by a holding device as the balloon catheter is inserted into the interior of the protective sheath.

One embodiment of the process further provides that a longitudinal axis of the balloon catheter (and, in particular, a longitudinal axis of the protective sheath) be vertically oriented as the balloon catheter moves. This vertical processing advantageously makes it possible to save clean room space.

One embodiment of the process further provides that a third and a fourth roller be used to guide the balloon catheter as it is inserted into the interior of the protective sheath, the third and fourth rollers being arranged so that they are displaced by 90° with respect to the first and second rollers in the peripheral direction of the balloon catheter or the protective sheath, in particular the third roller being pressed against the balloon catheter with a third film laid between them, and in particular the fourth roller being pressed against the balloon catheter with a fourth film laid between them.

One embodiment of the process further provides that the respective film be unwound from a feed roller as the balloon catheter is inserted into the interior of the protective sheath and wound up onto a take-up roller. To produce the aforementioned advancement of the respective film (see above), the respective take-up roller can be driven or rotated, e.g., by a drive.

Instead of rollers, it is also possible to use another system (a caterpillar track system, grippers, or something similar) to guide and/or move the balloon catheter.

One embodiment of the process further provides that the balloon catheter have a proximal end and an opposite distal end section, the drug-coated area being arranged at the distal end section of the balloon catheter, and the balloon catheter being inserted into the interior of the protective sheath with the proximal end first, or the protective sheath being arranged on the balloon catheter from proximal end of the balloon catheter.

One embodiment of the inventive process that represents an alternative especially with respect to the rollers provides that the aforementioned relative motion be produced with the help of a first and a second contact element, the two contact elements being movable out of a first position toward one another into a second position.

One embodiment of the process provides that after the balloon catheter is inserted into the interior of the protective sheath, the two contact elements be moved into the second position, so that the two contact elements reach behind one end of the protective sheath or grasp or hold one section of the protective sheath, the balloon catheter being held by a holding device, and the two contact elements being moved along the balloon catheter, which is at rest, carrying along the protective sheath, the protective sheath being pushed over the drug-coated area.

One alternative embodiment of the process further provides that after the balloon catheter is inserted into the interior of the protective sheath, the two contact elements be moved into the second position, so that the two contact elements grasp or hold one section of the balloon catheter outside the drug-coated area, the protective sheath being held by a holding device, and the two contact elements being moved away from the protective sheath, which is at rest, carrying along the balloon catheter, so that the drug-coated area is inserted into the interior of the protective sheath, in particular, pulled into the interior of the protective sheath.

To move the protective sheath or to move the balloon catheter, the contact elements can be moved in the horizontal direction (in this case the balloon catheter and the protective sheath extend horizontally) or in the vertical direction (in this case the balloon catheter and the protective sheath extend vertically).

The drug-coated area can be a drug-coated balloon of the balloon catheter, or a drug-coated stent of the balloon catheter that is crimped onto a balloon of the balloon catheter.

All embodiments of the process can further provide that as the protective sheath is arranged on the drug-coated area, the protective sheath is rotated with respect to the balloon catheter about a longitudinal axis of the protective sheath, or that as the protective sheath is arranged on the drug-coated area the balloon catheter is rotated with respect to the protective sheath about a longitudinal axis of the balloon catheter. This is especially advantageous if the drug-coated area is formed by the balloon of the balloon catheter, so that a folding of the balloon is not disturbed, i.e., is maintained as the protective sheath is pulled over.

The inventive protective sheath assembly can also be integrated into the balloon folding process: after folding, the catheter is pulled out of the folding system. This movement in combination with the holding device can also be used to assemble the protective sheath.

Another aspect of this invention relates to a device for arranging a protective sheath on a drug-coated area of a balloon catheter.

To arrange the protective sheath on the drug-coated area of the balloon catheter, the device is configured to produce a relative motion between the balloon catheter and the protective sheath, the device further having a first and a second film, which are configured to prevent contact between the drug-coated area and a guide of the device during the relative motion, the guide being designed to guide the balloon catheter, or the device being designed to hold the balloon catheter away from the drug-coated area during the relative motion.

According to one embodiment of the device, the guide has at least one first contact element and one second contact element that is opposite the first, the first contact element being pressable against the balloon catheter with the first film laid between them, and the second contact element being pressable against the balloon catheter with the second film laid between them. To accomplish this, one embodiment of the device provides that for the contact elements to press against the balloon catheter (with the respective film between), they be movable out of a first position toward one another into a second position, the two contact elements being configured so that in the second position they press against the balloon catheter (with the respective film between) and guide it.

One embodiment of the device further provides that the first contact element be a rotatable first roller, and that the second contact element be a rotatable second roller.

One embodiment of the device further provides that the device be configured to move the balloon catheter relative to the protective sheath by advancing the respective film, and/or by rotating the respective roller by a drive of the device.

One preferred embodiment of the device further provides that the first film be movable along the first roller with an advancement speed that corresponds to a rotational speed of the first roller, and the second film be movable along the second roller with an advancement speed that corresponds to a rotational speed of the second roller.

One embodiment of the device further provides that the device have a holding device that is designed to hold the protective sheath as the balloon catheter is inserted into the interior of the protective sheath.

One embodiment of the device further provides that the device have a third and a fourth roller to guide the balloon catheter as it is inserted into the interior of the protective sheath, the third and fourth rollers being arranged so that they are displaced by 90° with respect to the first and second rollers, in particular the third roller being pressable against the balloon catheter with a third film laid between them, and in particular the fourth roller being pressable against the balloon catheter with a fourth film of the device laid between them.

One embodiment of the device further provides that to unwind the respective film as the balloon catheter is inserted into the interior of the protective sheath, the device have a feed roller, and that the device have a take-up roller to wind up the respective film. To produce the aforementioned advancement of the respective film (see above), the device can be designed, e.g., to drive or rotate the respective take-up roller, e.g., by a drive.

An alternative embodiment of the device provides that the device be configured to produce the aforementioned relative motion with the help of a first and a second contact element of the device, the two contact elements being designed to be moved out of a first position toward one another into a second position.

One embodiment of the device further provides that these two contact elements be movable into the second position so that the two contact elements reach behind one end of the protective sheath or grip a section of the protective sheath if the balloon catheter is held as intended by a holding device. Furthermore, the two contact elements are preferably configured to be moved along the balloon catheter, carrying along the protective sheath, to push the protective sheath over the drug-coated area of the balloon catheter.

One embodiment of the device further provides that these two contact elements be movable into the second position to grip a section of the balloon catheter outside the drug-coated area, the two contact elements preferably being designed to be moved away from the protective sheath, which is at rest, carrying the balloon catheter along with them, if the protective sheath is held by a holding device of the device, in order to insert the drug-coated area into the interior of the protective sheath, in particular to pull the drug-coated area into the interior of the protective sheath.

One embodiment of the device further provides that the device be configured to rotate the protective sheath with respect to the balloon catheter about a longitudinal axis of the protective sheath as the protective sheath is arranged on the drug-coated area. Alternatively, the device can be designed to rotate the balloon catheter with respect to the protective sheath about a longitudinal axis of the balloon catheter as the protective sheath is arranged on the drug-coated area.

This invention advantageously allows machine positioning of a protective sheath on drug-coated balloons or stents and prevents cross contamination of the respective drug-coated area as this is done.

FIGS. 1 through 4 show different embodiments of a process or a device for arranging a protective sheath 2 on a drug-coated balloon catheter 3, the protective sheath 2 having a wall 20 circling in a peripheral direction U, this wall surrounding an interior 21 of the protective sheath 2, the process having at least the following step: Arranging the protective sheath 2 on a drug-coated area 30a of the balloon catheter 3 by machine production of a relative motion between the balloon catheter 3 and the protective sheath 2, the drug-coated area 30a of the balloon catheter 3 being protected, by at least one first and one second flexible film 5, 6, against coming in contact with a guide 4 for the balloon catheter 3 during the relative motion (see FIGS. 1 through 3), or the balloon catheter 3 being held away from the drug-coated area 30a during the relative motion (see FIG. 4).

The drug-coated area 30a can be the balloon 30 of the balloon catheter 3 (or a section of the balloon 30). Alternatively, the drug-coated area 30a can also be a stent 30b that sits on a balloon 30 of the balloon catheter 3. Such a balloon 30 or stent 30b can be used, e.g., in an angioplasty procedure to expand a vessel of a patient, or to hold it open. The balloon catheter 3 also has, in particular, an inner lumen 31 for deploying the balloon 30 and, in particular, X-ray markers 32.

In order to save space in a clean room in which the respective process is preferably carried out, the balloon catheters 3 can be processed in the vertical orientation (as shown in FIGS. 1 through 4). In particular, the protective sheath 2 is assembled after the respective balloon 30 is folded and fixed.

Figure 1A:
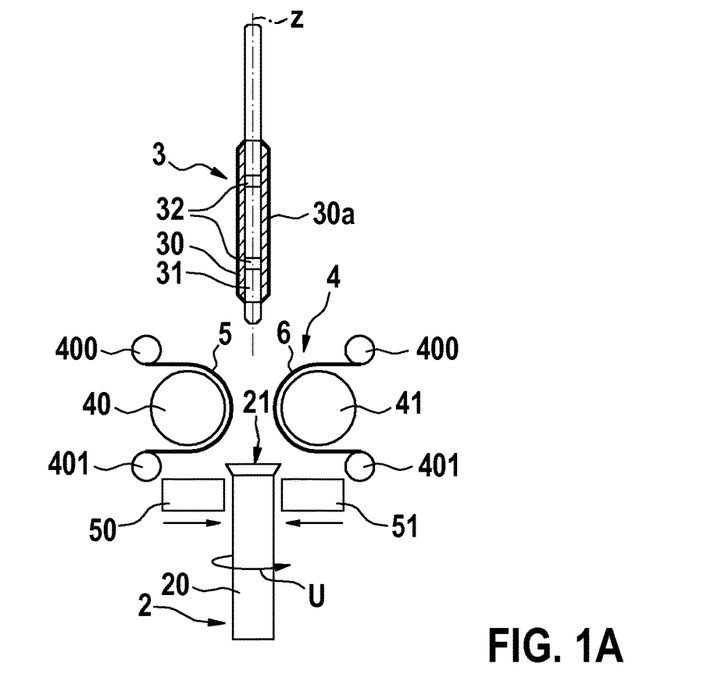
Figure 1B:
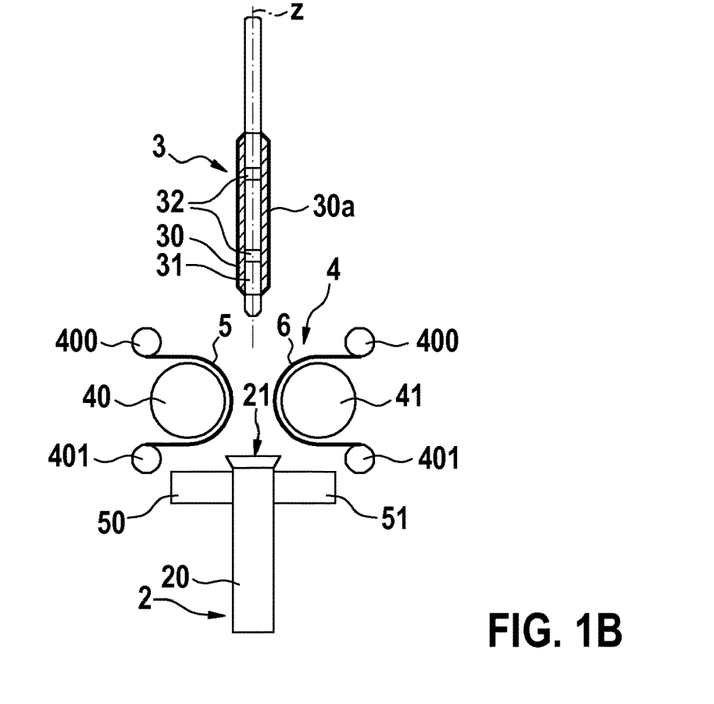
Figure 2A:
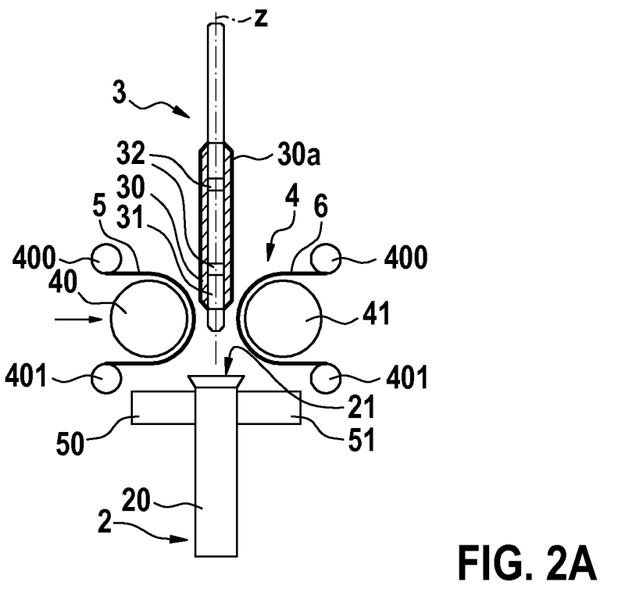
Figure 2B:
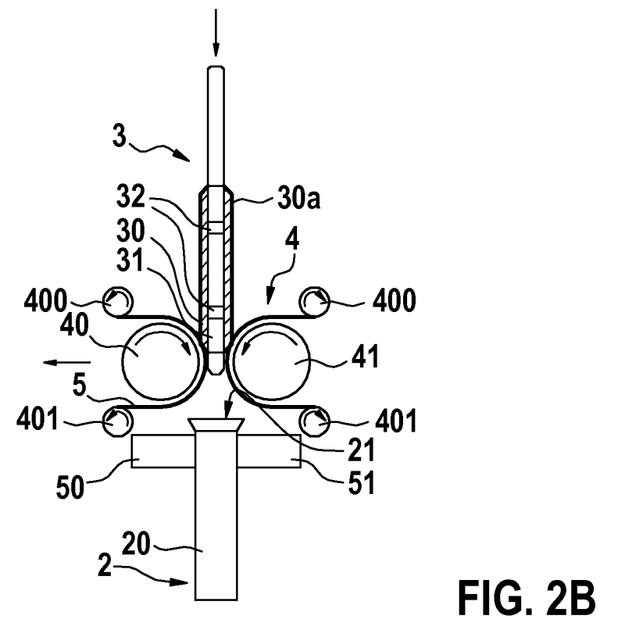
Figure 2C:
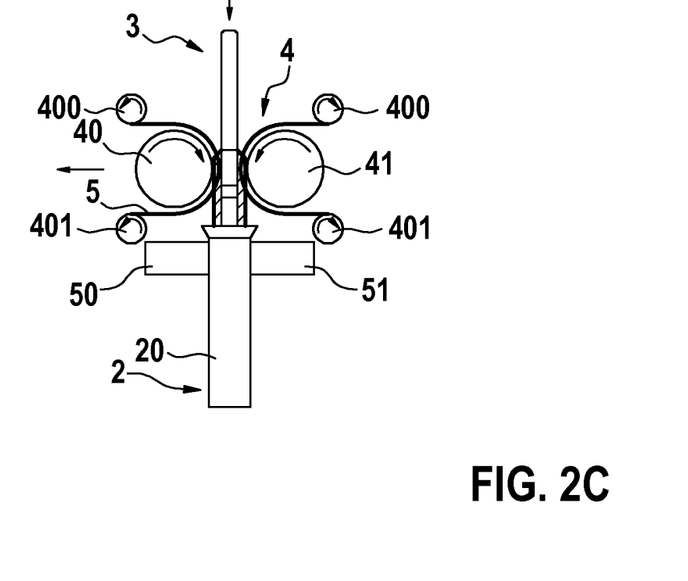
Figure 3A:
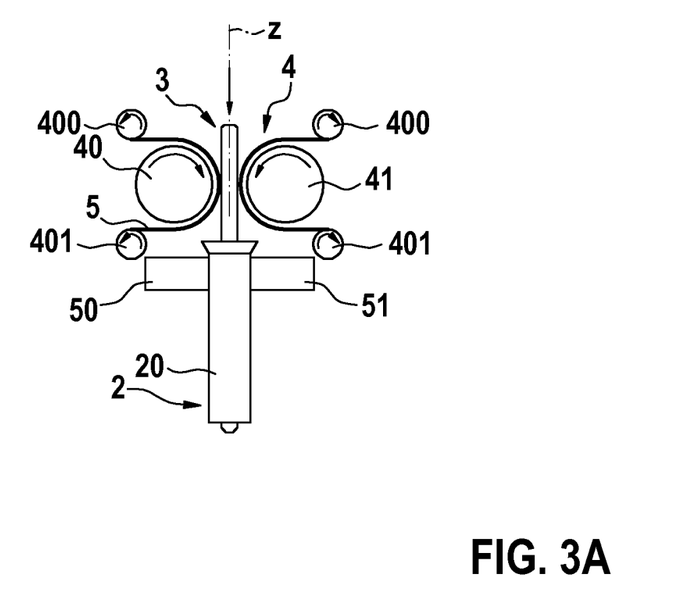
Figure 3B:
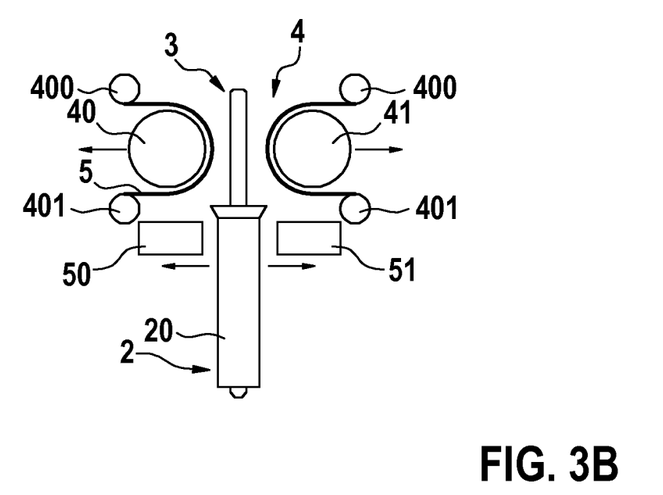
Figure 3C:
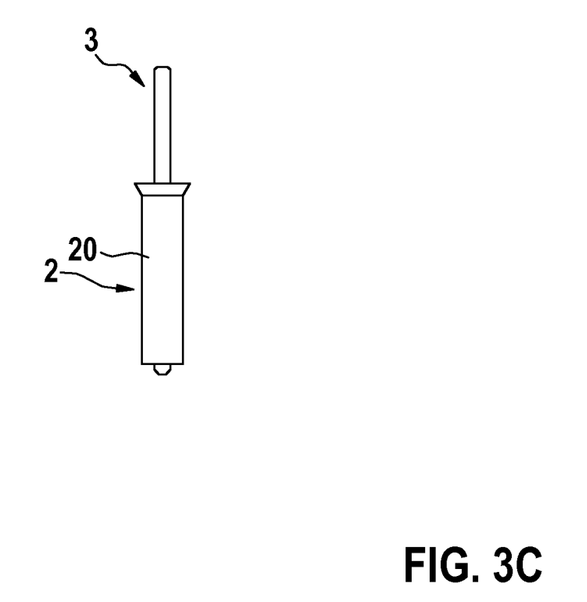

The protective sheath 2 can, e.g., be transported, via a transport system (e.g., having a slide or a linear axis, or something similar), into a holding device 50, 51 beneath the hanging balloon catheter 3 (see FIG. 1(A)). Next, the holding device 50, 51 fixes the protective sheath 2 (see FIG. 1(B)). To accomplish this, the holding device 50, 51 can have, e.g., two movable holding jaws 50, 51. Above the holding device 50, 51 there are two contact elements 40, 41 in the form of a first and a second roller 40, 41, which form a pair of rollers. The two rollers 40, 41 can be moved between a first position, in which the films 5, 6 do not lie against the catheter 3, into a second position (toward one another), in which the rollers 40, 41 press the respective film 5, 6 against the balloon catheter 3 and, accordingly, guide or advance the catheter 3 into the protective sheath 2. That is, the purpose of the roller pair 40, 41 is to push the balloon catheter 3 in a guided manner into the interior 21 of the protective sheath 2 (see FIG. 2(A) through FIG. 3(A)). As this is done, the rotational speed and the advancement speed of the catheter 3 are preferably synchronized. After the assembly step, the roller pair 40, 41 opens, i.e., the two contact elements 40, 41 are separated from one another, and the holding device 50, 51 and the catheter 3 are freed for the further processing (see FIG. 3(B) through 3(C)).

For the processing of drug-coated balloon catheters 3, the roller pair 40, 41 is, as can be seen from FIGS. 1(A) through 3(B), protected by retractable films 5, 6. The advancement speed of the respective film 5, 6 is preferably synchronized with the rotational speed of the respective roller 40, 41. This can ensure that the balloon catheter 3 always only comes in contact with the uncontaminated part of the film 5 or 6.

As can also be seen from FIGS. 1(A) through 3(B), as the balloon catheter 3 is inserted into the interior 21 of the protective sheath 2 the respective film 5, 6 can be unwound from a feed roller 400 and wound up onto a take-up roller 401. It is conceivable to make the catheter 3 move into the protective sheath 2 by advancing the respective film 5, 6, e.g., by rotating or driving the respective take-up roller 401 by a drive. Alternatively or additionally, the respective roller 40, 41 can be rotated by a drive. For the case in which the advancement is produced by the films 5, 6, the rollers 40, 41 only serve to guide the films 5, 6 or to provide them with contact pressure against the balloon catheter 3.

FIGS. 4(A) through 4(D) show an alternative embodiment of the inventive process or of an inventive device.

Figure 4A:
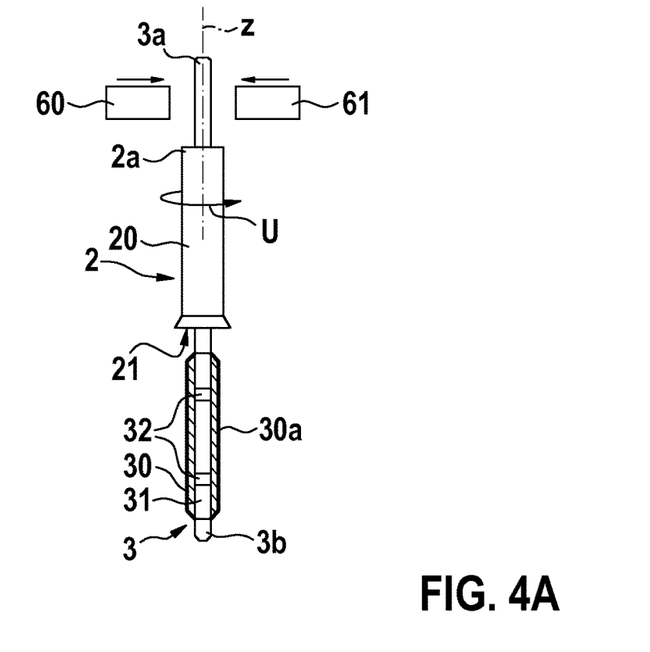

The balloon catheter 3 has a proximal end 3a and an opposite distal end section 3b, the drug-coated area 30 being arranged at the distal end section 3b of the balloon catheter 3, and the balloon catheter 3 first being inserted into the interior 21 of the protective sheath 2 with the proximal end 3a first, or alternatively the protective sheath 2 being arranged on the balloon catheter 3 from proximal end 3a of the balloon catheter 3 (see FIG. 4(A)). This step can take place, for example, before the assembly of a Luer connection or also before the drug coating itself.

Figure 4B:
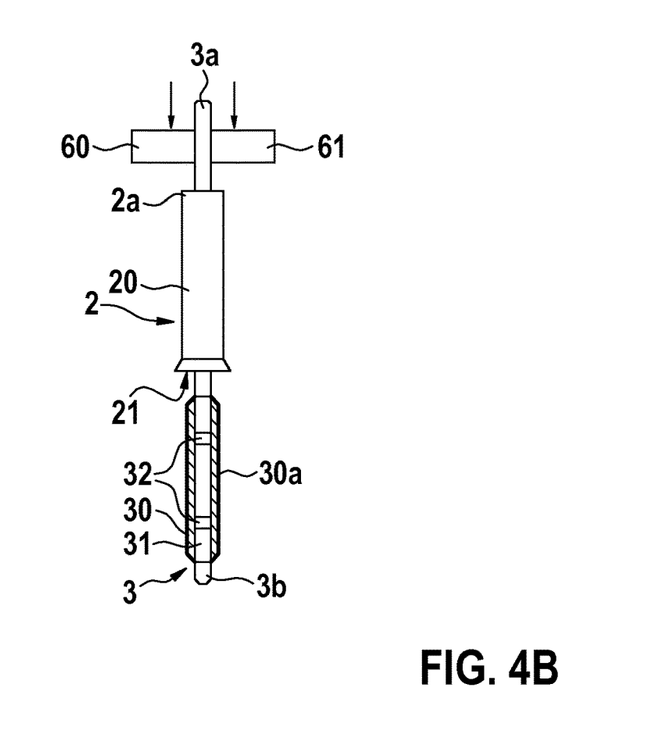

To push the protective sheath 2 down onto the drug-coated area 30a of the catheter 3, a first and a second contact element 60, 61 are now provided, which are movable out of a first position toward one another into a second position, in which the two contact elements 60, 61 reach behind one end 2a of the protective sheath 2 (see FIG. 4(B)).

Figure 4C:
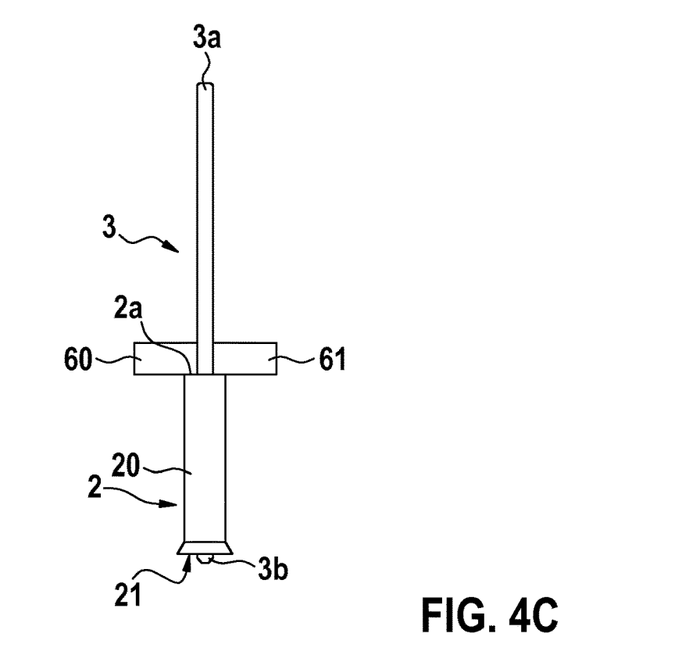
Figure 4D:
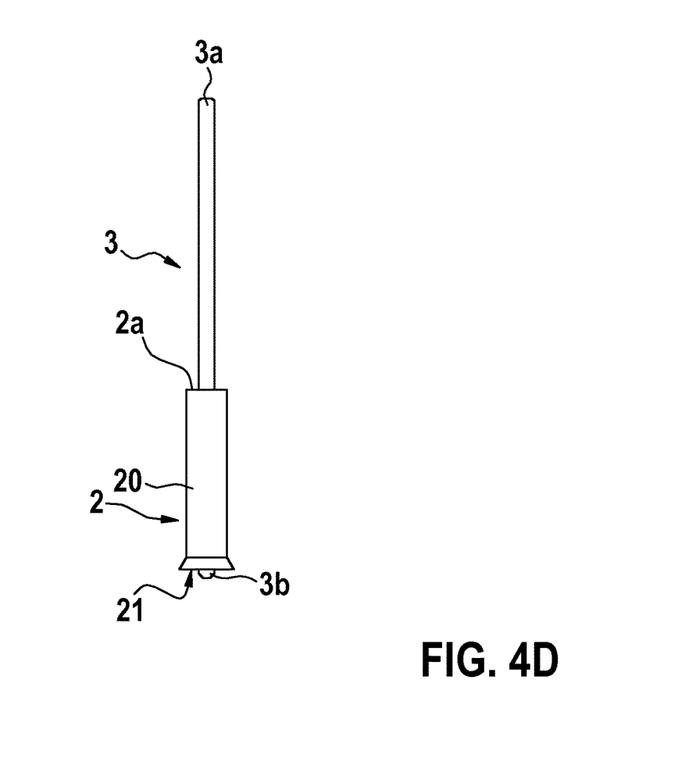

The balloon catheter 3 is held by a holding device (not shown), and the contact elements 60, 61 are now moved down along the catheter 3, and because the two contact elements 60, 61 reach behind the end 2a of the protective sheath 2 they press against it and carry it down along with them, pushing it onto the drug-coated area 30a (see FIG. 4(C)). After this, the balloon catheter 3, together with the protective sheath 2 arranged as intended, can be removed from the contact elements 60, 61 (see FIG. 4(D)) and possibly undergo further processing.

The invention claimed is:

1. A process for arranging a protective sheath on a drug-coated balloon catheter in a machine, the protective sheath having a wall circling in a peripheral direction and surrounding an interior of the protective sheath, the process comprising:
    transporting the protective sheath via a transport system into a holding device;
    protecting a drug coated area of the balloon catheter from contact with the machine; and
    arranging the protective sheath on a drug-coated area of the balloon catheter by machine relative motion between the balloon catheter and the protective sheath, wherein said protecting comprises one of placing at least one first and one second flexible film between the balloon catheter and a guide of the machine during the relative motion.

2. A process according to claim 1, wherein the guide has at least one first and one opposite second contact element, the first contact element being pressed against the balloon catheter with the first film between them, and the second contact element being pressed against the balloon catheter with the second film between them during said arranging.

3. A process according to claim 2, wherein the first contact element is a rotatable first roller and the second contact element is a rotatable second roller.

4. A process according to claim 3, wherein the balloon catheter is moved relative to the protective sheath by one or both of advancing the respective first and second films and rotating one or both of the first and second rollers with a drive.

5. A process according to claim 4, wherein the first film is moved along the first roller with an advancement speed that corresponds to a rotational speed of the first roller and the second film is moved along the second roller with an advancement speed that corresponds to a rotational speed of the second roller.

6. A process according claim 3, wherein the protective sheath is held by the holding device while the balloon catheter is inserted into the interior of the protective sheath during said arranging.

7. A process according to claim 1, wherein a longitudinal axis of the balloon catheter is vertically oriented during said arranging.

8. A process according to claim 6, wherein a third and a fourth roller with third and fourth films are used to guide the balloon catheter as it is inserted into the interior of the protective sheath, the third and fourth rollers being arranged so that they are displaced by 90° with respect to the first and second rollers in the peripheral direction of the balloon catheter.

9. A process according claim 8, wherein as the balloon catheter is inserted into the interior of the protective sheath the respective first through fourth films are each unwound from a feed roller and wound up onto a take-up roller.

10. A process according to claim 1, wherein the drug-coated area is a drug-coated balloon of the balloon catheter.

11. A process according to claim 1, wherein the drug-coated area is a drug-coated stent of the balloon catheter that is crimped onto a balloon of the balloon catheter.

12. A process for arranging a protective sheath on a drug-coated balloon catheter in a machine, the protective sheath having a wall circling in a peripheral direction and surrounding an interior of the protective sheath, the process comprising:
    transporting the protective sheath via a transport system into a holding device;
    protecting a drug coated area of the balloon catheter from contact with the machine; and
    arranging the protective sheath on drug-coated area of the balloon catheter by machine relative motion between the balloon catheter and the protective sheath, wherein said protecting comprises one of placing at least one first and one second flexible film between the balloon catheter and a guide of the machine during the relative motion, or holding the balloon catheter at a position on the catheter away from the drug-coated area during the relative motion, wherein the balloon catheter has a proximal end and an opposite distal end section, the drug-coated area being arranged at the distal end section, wherein said arranging comprises one of inserting the balloon catheter into the interior of the protective sheath with a proximal end of the balloon catheter first and arranging the protective sheath starting from the proximal end of the balloon catheter.

13. A process according to claim 12, wherein the relative motion is produced with a first and a second contact element, the first and second contact elements being movable out of a first position toward one another into a second position.

14. A process according to claim 13, wherein after the balloon catheter is inserted into the interior of the protective sheath, the first and second contact elements are moved into the second position and reach behind one end of the protective sheath or grip a section of the protective sheath, the two contact elements being moved along the balloon catheter carrying along the protective sheath to push it over the drug-coated area.

15. A process according to claim 12, wherein after the balloon catheter is inserted into the interior of the protective sheath, the first and second contact elements are moved into the second position so that the two contact elements grasp one section of the balloon catheter proximal of the drug-coated area, the two contact elements being moved away from the protective sheath carrying along the balloon catheter so that the drug-coated area is pulled into the interior of the protective sheath.

16. A process for arranging a protective sheath on a drug-coated balloon catheter in a machine, the protective sheath having a wall circling in a peripheral direction and surrounding an interior of the protective sheath, the process comprising:
    transporting the protective sheath via a transport system into a holding device;
    protecting a drug coated area of the balloon catheter from contact with the machine; and
    arranging the protective sheath on a drug-coated area of the balloon catheter by machine relative motion between the balloon catheter and the protective sheath, wherein said protecting comprises one of placing at least one first and one second flexible film between the balloon catheter and a guide of the machine during the relative motion, or holding the balloon catheter at a position on the catheter away from the drug-coated area during the relative motion, wherein as the protective sheath is arranged on the drug-coated area, the protective sheath is rotated with respect to the balloon catheter about a longitudinal axis of the protective sheath or the balloon catheter is rotated with respect to the protective sheath about the longitudinal axis.

17. A process for arranging a protective sheath on a drug-coated balloon catheter in a machine, the protective sheath having a wall circling in a peripheral direction and surrounding an interior of the protective sheath, the process comprising:
- transporting the protective sheath via a transport system into a holding device;
- gripping one of the protective sheath and the balloon catheter with a movable machine part while protecting a drug coated area of the balloon catheter from contact with the machine part; and
- moving the movable machine part to insert the balloon catheter into the protective sheath, wherein the movable machine part moves the balloon catheter via a protective film pressed between the movable machine part and the balloon catheter or the movable machine part moves the protective sheath by reaching behind an end of the protective sheath and pressing against the end of the protective sheath to push the protective sheath onto the drug-coated area of the balloon catheter.

* * * * *